(12) United States Patent
Dunkern et al.

(10) Patent No.: US 7,666,872 B2
(45) Date of Patent: Feb. 23, 2010

(54) USE FOR PDE5 INHIBITORS

(75) Inventors: Torsten Dunkern, Stockach (DE); Christian Schudt, Constance (DE); Friedrich Grimminger, Butzbach (DE); Hossein Ardeschir Ghofrani, Giessen (DE); Manfred Kaps, Wetzlar (DE); Bernhard Rosengarten, Giessen (DE)

(73) Assignee: NYCOMED GmbH, Constance (DE)

( * ) Notice: Subject to any disclaimer, the term of this patent is extended or adjusted under 35 U.S.C. 154(b) by 110 days.

(21) Appl. No.: 10/590,992

(22) PCT Filed: Mar. 3, 2005

(86) PCT No.: PCT/EP2005/050958

§ 371 (c)(1), (2), (4) Date: Sep. 27, 2006

(87) PCT Pub. No.: WO2005/089766

PCT Pub. Date: Sep. 29, 2005

(65) Prior Publication Data

US 2007/0185114 A1 Aug. 9, 2007

(30) Foreign Application Priority Data

Mar. 5, 2004 (EP) .................................. 04100909

(51) Int. Cl.
*A61K 31/496* (2006.01)
(52) U.S. Cl. .................................. 514/252.16
(58) Field of Classification Search ........................ None
See application file for complete search history.

(56) References Cited

FOREIGN PATENT DOCUMENTS

| EP | 0 758 653 A1 | 2/1997 |
|----|--------------|--------|
| EP | 0 985 671 A1 | 3/2000 |
| EP | 1 317 924 A1 | 6/2003 |
| WO | 98/38168 A1 | 9/1998 |
| WO | 01/27112 A1 | 4/2001 |
| WO | 02/089808 A1 | 11/2002 |
| WO | 03/051346 A2 | 6/2003 |

OTHER PUBLICATIONS

Wratten, European Journal of Anaesthesiology (2008) 25 (Suppl. 42):1-7.*
Wratten, European Journal of Anaesthesiology (2008) 25 (Suppl. 42): 1-7.*
Wilson (Neurol. J. Southeast Asia (2003) 8:65-76).*
Bischoff (International Journal of Impotence Research (2004) 16:S1-S14).*
Ghofrani, H.A., et al., "Sildenafil for treatment of lung fibrosis and pulmonary hypertension: a randomised controlled trial", *The Lancet*, vol. 360, p. 895-900, (2002).

Ghofrani, H.A., et al., "Oral Sildenafil as Long-Term Adjunct Therapy to Inhaled Iloprost in Severe Pulmonary Arterial Hypertension", *Journal of the American College of Cardiology*, vol. 42, No. 1, p. 158-164, (2003).
Ghofrani, H.A., et al., "Sildenafil for Long-Term Treatment of Nonoperable Chronic Thromboembolic Pulmonary Hypertension", *Am J Respir Crit Care Med*, vol. 167, p. 1139-1141, (2003).
Cunningham, D,R., et al., "The Effects of Chronic Hypoxemia on Central Auditory Processing in Patients with Chronic Obstructive Pulmonary Disease", *Ear and Hearing*, vol. 6, No. 6, p. 297-303, (1985).
Bianco, A., et al., "Effect of Sildenafil on Diabetic Gastropathy", *Diabetes Care*, vol. 25, No. 10, p. 1188-1889, (2002).
Barnes, P.J., "Cyclic nucleotides and phosphodiesterases and airway function", *Eur Respir J*, vol. 8, p. 457-462, (1995).
Halcox, J.P.J., et al., "The Effect of Sildenafil on Human Vascular Function, Platelet Activation, and Myocardial Ischemia", *Journal of American College of Cardiology*, vol. 40, No. 7, p. 1232-1240, (2002).
Presberg, K.W., et al., "Pathophysiology of pulmonary hypertension due to lung disease", *Current Opinion in Pulmonary Medicine*, vol. 9, p. 131-138, (2003).
Prasad, S., et al., "Sildenafil in Primary Pulmonary Hypertension", *The New Enland Journal of Medicine*, vol. 343:1342, No. 18, p. 1-3, (2000).
Nehra, A., et al., "Sildenafil citrate, a selective phosphodiesterase type 5 inhibitor: urologic and cardiovascular implications", *World J Urol*, vol. 19, p. 40-45, (2001).
Michelakis, E.D., et al., "Long-Term Treatment With Oral Sildenafil Is Safe and Improves Functional Capacity and Hemodynamics in Patients With Pulmonary Arterial Hypertension", *Circulation*, vol. 108, p. 2066-2069, (2003).
Kruuse, C., et al., "Migraine can be induced by sildenafil without changes in middle cerebral artery diameter", *Brain*, vol. 126, p. 241-247, (2003).
Prickaerts, J., et al., "Effects of Two Selective Phosphodiesterase Type 5 Inhibitors, Sildenafil and Vardenafil, an Object Recognition Memory and Hippocampal Cyclic GMP Levels in the Rat", *Neuroscience*, vol. 113, No. 2, p. 351-361, (2002).
Incalzi, R.A., et al., "Cognitive impairment in chronic obstructive pulmonary disease: A neuropsychological and spect study", *J Neurol*, vol. 250, p. 325-332, (2003).
Watkins, C.C., et al., "Insulin restores neuronal nitric oxide synthase expression and function that is lost in diabetic gastropathy", *The Journal of Clinical Investigation*, vol. 106, No. 3, p. 373-384, (2000).
Zhang, R., et al., "Sildenafil (Viagra) Induces Neurogenesis and Promotes Functional Recovery After Stroke in Rats", *Stroke*, vol. 33, p. 2675-2680, (2002).
Zhang, R., et al., "Nitric Oxide Enhances Angiogenesis via the Synthesis of Vascular Endothelial Growth Factor and cGMP After Stroke in the Rat", *Circ Res.*, vol. 92, p. 308-313, (2003).
Yamamoto, T., et al., "Chronic administration of phosphodiesterase type 5 inhibitor suppresses renal production of endothelin-1 in dogs with congestive heart failure", *Clinical Science*, vol. 103 (Suppl. 48), p. 2585-2625, (2002).

(Continued)

*Primary Examiner*—Frederick Krass
*Assistant Examiner*—Marcos Sznaidman
(74) *Attorney, Agent, or Firm*—The Nath Law Group; Joshua B. Goldberg; Sheldon M. McGee

(57) ABSTRACT

The present invention is concerned with the use of PDE5 inhibitors in medicine.

1 Claim, 3 Drawing Sheets

OTHER PUBLICATIONS

Reffelmann, T., et al, "Therapeutic Potential of Phosphodiesterase 5 Inhibition for Cardiovascular Disease", *Circulation*, vol. 108, p. 239-244, (2003).

Lehmann et al., Effects of activated protein C on the mesenteric microcirculation and cytokine release during experimental endotoxemia, *Can. J. Anesth. 2008*, 55:3, pp. 155-162.

Lehmann et al., Activated protein C improves intestinal microcirculation in experimental endotoxaemia in the rat, *Critical Care*, 2006, 10:R157.

Gupta et al., Activated protein C ameliorates LPS-induced acute kidney injury and down-regulates renal iNOS and angiotensin 2, *Am. J. Physiol. Renal Physiol.*, 2007, Jul. 293(1) F245-54, Epub 2007.

\* cited by examiner

USE FOR PDE5 INHIBITORS

This application was filed under 35 U.S.C. 371 as a national stage of PCT/EP2005/050958, filed Mar. 3, 2005.

TECHNICAL FIELD

The present invention is concerned with phosphodiesterase-5 inhibitors and the use of such compounds in medicine, particularly in the treatment of diseases, which are associated with or characterized by cerebrate maldistribution of the blood or impaired reagibility of the blood flow in the brain.

PRIOR ART

The 3',5'-cyclic nucleotide phosphodiesterases (PDEs) comprise a large class of enzymes divided into at least eleven different families which are structurally, biochemically and pharmacologically distinct from one another. The enzymes within each family are commonly referred to as isoenzymes, or isozymes. Further diversity among the isoenzymes results from differential splicing and post-translational processing of those gene products.

PDE5s are characterized by selective, high affinity hydrolytic degradation of the second messenger cyclic nucleotide, guanosine 3',5'-cyclic monophosphate (cGMP). Barnes et al. [Barnes P J et al. (1995) Eur. Resp. J. 8: 457] describe the involvement of PDE5 in the degradation of cGMP in smooth muscle cells of the airways and vessels.

A whole series of PDE5 inhibiting substances are known from the prior art and are described as potent and effective substances for the treatment of erectile dysfunction. E.g. the PDE5-inhibitors sildenafil, vardenafil and tadalafil are commercially available for the treatment of erectile dysfunction. By inducing relaxation of the vasculature within the corpus cavernosum of the penis, they increase the blood flow, thereby inducing tuminescence of the penis. Relaxation of the vasculature is initiated by the release of NO from adrenergic neurons which subsequently activates the guanylyl cyclase of smooth muscle cells of the vessels of the corpus cavernosum. Once activated guanylyl cyclase synthesizes the second messenger cGMP which mediates the relaxation of the cell. PDE5-inhibitors prevent the degradation of cGMP by phosphodiesterase-5, thereby prolonging and enhancing the effects of cGMP. Due to its effects on relaxation of blood vessels PDE5-inhibitors have been proposed to be an "ideal" drug for other clinical indications. Thus it has been demonstrated in several animal models and recently in several clinical trials that PDE5-inhibitors reduce the symptoms of pulmonary hypertension and commencing right-heart failure [Michelakis et al. (2003) Circulation 108: 2066; Ghofrani et. al (2003) J Am Coll Cardiol 42: 158; Ghofrani et al. (2002) Lancet 360: 895; Ghofrani et al. (2003) AJRCCM 167(8): 1139]. Furthermore—despite the fact that the mode of action is not clear—it has been shown that the PDE-5-inhibitor sildenafil (Viagra®) induces neurogenesis and promotes functional recovery after stroke in rats [Zhang et al. (2002) Stroke 33: 2675-2680; Zhang et al (2003) Circ. Res. 92(3): 308]. In a dog model of congestive heart failure it has been shown that chronic administration of a phosphodiesterase type 5 inhibitor suppresses renal production of endothelin-1 [Yamamoto et al. (2002) Clin Sci (Lond.) 103: 258S]. In addition sildenafil has been shown to relax epicardial coronary arteries of patients with coronary artery disease [Halcox et al. (2002) J Am Coll Cardiol 40: 1232] and some animal studies suggest that sildenafil might work in diabetic gastropathy (Bianco et al. (2002) Diabetes Care 25: 1888) in which nNOS expression and activity seems to be reduced (Watkins et al. (2000) J Clin Invest 106: 373). PDE5-inhibitors are suggested to be used in several indications as female sexual arousal disorder, angina and congestive heart failure [Nehra et al. (2001) World J Urol. 19(1): 115; Reffelmann et al. Circulation (2003) 108(2): 239).

EP 10977911 discloses that sildenafil and other PDE5-inhibiting substances can be employed for the treatment of pulmonary hypertension and Prasad et al. [Prasad et al. (2000) New England Journal of Medicine 343: 1342] postulate a beneficial role of sildenafil in primary pulmonary hypertension. EP 758653 discloses that PDE5 inhibitors are useful for treating bronchitis, chronic asthma, and hypertension.

In WO 03/051346 the use of PDE5-inhibitors as a "rematching" drug especially in COPD-patients has been described. This means that PDE5-inhibitors improve the spatial balance between blood perfusion and ventilation within the lung thereby reducing the amount of so-called low V/Q-areals (meaning high perfusion but no or reduced ventilation) and high V/Q-areals (meaning low perfusion but high ventilation). This "re-matching"-mechanism is being extended to other diseases such as asthma and diabetes mellitus.

In spite of the fact that effects of the PDE5-inhibitors sildenafil and vardenafil on object recognition memory of rats (Prickaerts J, van Staveren W C, Sik A, Markerink-van Ittersum M, Niewohner U, van der Staay F J, Blokland A, de Vente J. Effects of two selective phosphodiesterase type 5 inhibitors, sildenafil and vardenafil, on object recognition memory and hippocampal cyclic GMP levels in the rat. Neuroscience. 2002; 113(2):351-61) and on auditory selective attention and verbal recognition of healthy humans has been described no differences in brain perfusion e.g. blood flow velocity of the right middle cerebral artery after phosphodiesterase-5 treatment has been demonstrated. Also, sildenafil induced migraine could not be correlated with a changed cerebral blood flow (Kruuse C, Thomsen L L, Birk S, Olesen J. Migraine can be induced by sildenafil without changes in middle cerebral artery diameter. Brain. 2003 January; 126(Pt 1):241-7).

Hypoxemic COPD patients, which are known to develop secondary pulmonary hypertension (Presberg K W, Dincer H E. Pathophysiology of pulmonary hypertension due to lung disease. Curr Opin Pulm Med. 2003 March; 9(2):131-8) have been shown to be impaired besides their lung function in their cognitive abilities as verbal attainment, attention, deductive thinking and central auditory processing (Antonelli Incalzi R, Marra C, Giordano A, Calcagni M L, Cappa A, Basso S, Pagliari G, Fuso L. Cognitive impairment in chronic obstructive pulmonary disease—a neuropsychological and spect study. J Neurol. 2003 March; 250(3):325-32; Cunningham D R, Cunningham C A, Vise L K. The effects of chronic hypoxemia on central auditory processing in patients with chronic obstructive pulmonary disease. Ear Hear. 1985 November-December; 6(6):297-303.) In addition a reduced perfusion of cortical areas has been described in such patients (Antonelli et al., 2003). Up to now the therapy of such patients is limited to a restricted, small improvement in lung-function whereas no therapy is available to treat the symptoms described above, which are associated with impaired skills of the brain. Impaired brain skills based on the reduced ability of the cerebral vasculature to provide with an adequate perfusion can be associated besides COPD with a variety of diseases as e.g. primary or thromboembolic pulmonary hypertension or diabetes mellitus.

EP 1 317 924, EP 0985 671, WO 01/27 112, WO 98/38168, WO 02/89808 and Circulation Research, vol. 92, no. 3, p.

308-313 describe the abilities of PDE5 inhibitors to function other than by improving cerebral vascular reactivity in the meaning of this invention.

DESCRIPTION OF THE INVENTION

Prostaglandins and nitric oxide play a pivotal role in the regulation of macro- and microcirculatory blood flow distribution. Interference with both mediator systems can be associated with cerebrovascular dysfunction. Selectivity for the pulmonary circulation has been proven for both inhaled iloprost (long acting prostacyclin analogue) and for the oral phosphodiesterase-5 inhibitor sildenafil in the treatment of patients with chronic pulmonary hypertension. Both substances provoked significant reduction of pulmonary arterial pressure and vascular resistance. Despite equipotent systemic and pulmonary reactions of iloprost and sildenafil surprisingly opposite effects were observed regarding cerebral vascular tone: with sildenafil cerebral microvascular reactivity was significantly improved (towards normalization) while it gradually worsened with iloprost.

The present invention thus is related to the novel use of PDE5 inhibitors in the treatment or prophylaxis of diseases associated with or based on impairment or dysfunction of neurovascular coupling. Neurovascular coupling describes the phenomenon of regulation of regional microvascular perfusion upon neuronal demand (e.g. regional brain activity).

According to this invention, "PDE5 inhibitor" refers to a selective PDE inhibitor, which inhibits preferentially the type 5 phosphodiesterase (PDE5) when compared to other known types of phosphodiesterase, e.g. type 1, 2, 3, 4, etc. (PDE1, PDE2, PDE3, PDE4, etc.). According to this invention, a PDE inhibitor preferentially inhibiting PDE5 refers to a compound having a lower $IC_{50}$ for PDE5 (i.e. the $IC_{50}$ for PDE5 inhibition is about 10 times lower than the $IC_{50}$ for inhibition of other known types of phosphodiesterase, e.g. type 1, 2, 3, 4, etc.) and therefore is more potent to inhibit PDE5.

Methods to determine the activity and selectivity of a phosphodiesterase inhibitor are known to the person skilled in the art. In this connection it may be mentioned, for example, the methods described by Thompson et al. (Adv Cycl Nucl Res 10: 69-92, 1979), Giembycz et al (Br J Pharmacol 118: 1945-1958, 1996) and the phosphodiesterase scintillation proximity assay of Amersham Pharmacia Biotech.

Substances which may be included among PDE5 inhibitors for example are those described and claimed in the following patent applications and patents: WO 9626940, WO 9632379, EP 0985671, WO 9806722, EP 0012504, EP 0667345, EP 0579496, WO 9964004, WO 9605176, WO 9307124, WO 9900373, WO 9519978, WO 9419351, WO 9119717, EP 0463756, EP 0293063, WO 0012503, WO 9838168, WO 9924433, DE 3142982 and U.S. Pat. No. 5,294,612.

Compounds which may be mentioned as examples of PDE5 inhibitors are 3-ethyl-8-[2-(4-morpholinylmethyl) benzylamino]-2,3-dihydro-1H-imidazo[4,5-g]quinazoline-2-thione, 1-(2-chlorobenzyl)-3-isobutyryl-2-propylindole-6-carboxamide, 9-bromo-2-(3-hydroxypropoxy)-5-(3-pyridylmethyl)-4H-pyrido[3,2,1-jk]-carbazol-4-one, 4-(1,3-benzodioxol-5-ylmethylamino)-2-(1-imidazolyl)-6-methylthieno[2,3-d]pyrimidine, 6-(2-isopropyl-4,5,6,7-terahydropyrazolo[1,5-a]pyridin-3-yl)-5-methyl)-5-methyl-2,3,4,5-tetrahydropyridazin-3-one, 5-(4-methylbenzyl)-3-(1-methyl-4-phenylbutyl)-3,6-dihydro-[1,2,3]triazolo[4,5-d] pyrimidin-7-one, 3-(1-methyl-4-phenylbutyl)-5-pyridin-4-ylmethyl-3,6-dihydro-[1,2,3]triazolo[4,5-d]pyrimidin-7-one, 5-(4-bromobenzyl)-3-(1-methyl-4-phenylbutyl)-3,6-dihydro-[1,2,3]triazolo[4,5-d]pyrimidin-7-one, 5-benzyl-3-(1-methyl-4-phenylbutyl)-3,6-dihydro-[1,2,3]triazolo[4,5-d] pyrimidin-7-one, 5-(3,4-dimethoxybenzyl)-3-(1-methyl-4-phenylbutyl)-3,6-dihydro-[1,2,3]triazolo-[4,5-d]pyrimidin-7-one, 5-(3,4-dichlorobenzyl)-3-(1-methyl-4-phenylbutyl]3, 6-dihydro-[1,2,3]triazolo[4,5-d]pyrimidin-7-one, 5-biphenyl-4-ylmethyl-3-(1-methyl-4-phenylbutyl)-3,6-dihydro-[1,2,3]triazolo[4,5-d]pyrimidin-7-one, 5-(4-aminobenzyl)-3-(1-methyl-4-phenylbutyl]3,6-dihydro-[1,2,3] triazolo[4,5-d]pyrimidin-7-one, 5-(hydroxyphenylmethyl, 3-(1-methyl-4-phenylbutyl)-3,6-dihydro-[1,2,3]triazolo-[4, 5-d]pyrimidin-7-one, 5-benzo[1,3]dioxol-5-ylmethyl-3-[1-methyl-4-phenylbutyl)-3,6-dihydro-[1,2,3]triazolo[4,5-d] pyrimidin-7-one, N-4-[3-(1-methyl-4-phenylbutyl)-7-oxo-6, 7-dihydro-3H-[1,2,3]triazolo-[4,5-d]pyrimidin-5-ylmethyl] phenylacetamide, 5-benzoyl-3-(1-methyl-4-phenylbutyl)-3, 6-dihydro-[1,2,3]triazolo[4,5-d]-pyrimidin-7-one, 3-(1-methyl-4-phenylbutyl)-5-[4-(morpholine-4-sulphinyl) benzyl]-3,6-dihydro[1,2,3]triazolo[4,5-d]pyrimidin-7-one, 3-(1-methyl-4-phenylbutyl)-5-[3-(morpholine-4-sulphonyl) benzyl]-3,6-dihydro[1,2,3]triazolo[4,5-d]pyrimidin-7-one, N-methyl-4-[3-(1-methyl-4-phenylbutyl)-7-oxo-6,7-dihydro-3H-[1,2,3]-triazolo-[4,5-d]pyrimidin-5-ylmethyl]-benzenesulphonamide, N-(2-dimethylaminoethyl)-4-[3-(1-methyl-4-phenylbutyl)-7-oxo-6,7-dihydro-3H-1,2,3]triazolo[4, 5-d]pyrimidin-5-ylmethyl]benzenesulphonamide, N-(2-hydroxyethyl)-4-[3-(1-methyl-4-phenylbutyl)-7-oxo-6,7-dihydro-3H-[1,2,3]triazolo[4,5-d]pyrimidin-5-ylmethyl] benzenesulphonamide, ethyl 1-[3-[3-(1-methyl-4-phenylbutyl)-7-oxo-6,7-dihydro-3H-[1,2,3]-triazolo-[4,5-d] pyrimidin-5-ylmethyl]benzenesulphonyl] piperidinecarboxylate, 3-(1-methyl-4-phenylbutyl)-5-[4-(4-methylpiperazin-1-sulphonyl)benzyl]-3,6-dihydro-[1,2,3] triazolo[4,5-d]pyrimidin-7-one, 5-benzo[1,3]dioxol-5-ylmethyl-3-[1-ethy-heptyl]-3,6-dihydro-[1,2,3]-triazolo[4, 5-d]pyrimidin-7-one, 3-[1-(1-hydroxyethyl)-4-phenylbutyl]-5-[4-(morpholine-4-sulphonyl)benzyl]-3,6-dihydro-[1,2,3]triazolo[4,5-d]pyrimidin-7-one, 5-[6-fluoro-1-(phenylmethyl)-1H-indazol-3-yl]-2-furanmethanol, 1-benzyl-6-fluoro-3-[5-(hydroxymethyl)furan-2-yl]-1H-indazole, 2-(1H-imidazol-1-yl)-6-methoxy-4-(2-methoxyethylamino)quinazoline, 1-[[3-(7,8-dihydro-8-oxo-1H-imidazo[4,5-g]quinazolin-6-yl)-4-propoxyphenyl]sulphonyl]-4-methylpiperazine, 4-(3-chloro-4-methoxybenzylamino)-1-(4-hydroxypiperidin-1-yl)phthalazine-6-carbonitrile, 1-[6-chloro-4-(3,4-methylendioxybenzylamino)quinazolin-2-yl] piperidin-4-carboxylic acid, (6R,12aR)-6-(1,3-benzodioxol-5-yl)-2-methyl-1,2,3,4,6,7,12,12a-octa-hydropyrazino[2',1': 6,1]pyrido[3,4-b]indole-1,4-dione (tadalafil), (6R,12aR)-2, 3,6,7,12,12a-hexahydro-2-methyl-6-(3,4-methylenedioxyphenyl)-pyrazino-[2',1':6,1]pyrido[3,4-b] indole-1,4-dione, 4-ethoxy-2-phenylcycloheptylimidazole, (6-bromo-3-methoxymethylimidazo[1,2-a]pyrazin-8-yl)methylamine, 8-[(phenylmethyl)thio]-4-(1-morpholinyl)-2-(1-piperazinyl)pyrimidino[4,5-d]pyrimidine, (+)-cis-5-methyl-2-[4-(trifluoromethyl)benzyl]-3,4,5,6a,7,8,9-octahydrocyclopent[4,5]imidazo[2,1-b]purin-4-one, cis-2-hexyl-5-methyl-3,4,5,6a,7,8,9,9a-octahydrocyclopent[4,5] imidazo[2,1-b]purin-4-one, 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), 1-[[3-(6,7-dihydro-1-methyl-7-oxo-3-propyl-1H-pyrazolo[4,3-d]pyrimidin-5-yl)-4-ethoxyphenyl]sulfonyl]-4-methylpiperazine, 2-(2-propoxyphenyl)purin-6(1H)-one, 2-(2-propoxyphenyl)-1,7-dihydro-5H-purin-6-one, methyl 2-(2-methylpyridin-4-ylmethyl)-1-oxo-8-(2-pyrimidinylmethoxy)-4-(3,4,5-trimethoxyphenyl)-1,2-dihydro-[2,7]naphthyridin-3-carboxylate, methyl 2-(4- aminophenyl)-1-oxo-7-(2-pyridinylmethoxy)-4-(3,4,5-trimethoxyphenyl)-1,2-dihydroisoquinoline-3-carboxylate, 2-[2-ethoxy-5-(4-ethylpiperazin-1-ylsulfonyl)phenyl]-5-methyl-7-propylimidazo[5,1-f][1,2,4]triazin-4-(3H)-one (vardenafil), 3,4-dihydro-6-[4-(3,4-dimethoxybenzoyl)-1-piperazinyl]-2(1H)-quinolinone (vesnarinone), 1-cyclopentyl-3-methyl-6-(4-pyridyl)pyrazolo[3,4-d]pyrimidin-4(5H)-one, 1-cyclopentyl-6-(3-ethoxy-4-pyridinyl)-3-ethyl-1,7-dihydro-4H-pyrazolo[3,4-d]-pyrimidin-4-one, 6-o-propoxyphenyl-8-azapurin-6-one, 3,6-dihydro-5-(o-propoxyphenyl)-7H-v-triazolo[4,5-d]pyrimidin-7-one and 4-methyl-5-(4-pyridinyl)thiazole-2-carboxamide and the pharmaceutically acceptable derivatives of these compounds.

In the context of the present invention, unless otherwise stated, a pharmaceutically acceptable derivative of an active compound means a pharmaceutically acceptable salt or solvate (e.g. hydrate), a pharmaceutically acceptable solvate of such salt, a pharmaceutically acceptable N-oxide or a pharmaceutically acceptable salt or solvate of the latter.

PDE5 inhibitors, which are preferred in connection with the invention are compounds selected from the group tadalafil, sildenafil, vardenafil, UK357903, E4010, E8010 and TA-1790, DA-8159 and solvates, polymorphs and/or the pharmacologically acceptable salts of these compounds.

A preferred PDE5 inhibitor is sildenafil (which is 5-[2-ethoxy-5-(4-methylpiperazin-1-ylsulfonyl)phenyl]-1,6-dihydro-1-methyl-3-propylpyrazolo[4,3-d]pyrimidin-7-one), a pharmaceutically acceptable salt of sildenafil or a solvate of the pharmaceutically acceptable salt of sildenafil. In a preferred embodiment the PDE5 inhibitor is sildenafil citrate {the compound [1-[[3-(6,7-dihydro-1-methyl-7-oxo-3-propyl-1H-pyrazolo[4,3-d]pyrimidin-5-yl)-4-ethoxyphenyl]sulfonyl]-4-methylpiperazine citrate. The preparation of sildenafil is disclosed in EP 0463756.

Another preferred PDE5 inhibitor is vardenafil [which is 1-{[3-(3,4-Dihydro-5-methyl-4-oxo-7-propylimidazo[5,1-f]-as-triazin-2-yl)-4-ethoxyphenyl]sulfonyl}-4-ethylpiperazine], a pharmaceutically acceptable salt of vardenafil or a solvate of the pharmaceutically acceptable salt of vardenafil. Examples of pharmaceutically acceptable salts of vardenafil are vardenafil hydrochloride, the trihydrate of vardenafil hydrochloride and vardenafil dihydrochloride. Vardenafil is known from WO99/24433.

Another preferred PDE5 inhibitor is tadalafil [which is (6R,12aR)-2,3,6,7,12,12a-Hexahydro-2-methyl-6-[3,4-(methylenedioxy)phenyl]pyrazino[1',2':1,6]pyrido[3,4-b]indole-1,4-dione], a pharmaceutically acceptable salt of tadalafil or a solvate of the pharmaceutically acceptable salt of tadalafil. Tadalafil is known from WO95/19978.

According to this invention, suitable pharmaceutically acceptable salts refer to water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic add, maleic acid, lauric acid, malic acid, fumaric acid, succinic acid, oxalic acid, tartaric acid, embonic acid, stearic acid, toluenesulfonic acid, methanesulfonic acid or 1-hydroxy-2-naphthoic acid, the acids being employed in salt preparation—depending on whether it is a mono- or polybasic acid and depending on which salt is desired—in an equimolar quantitative ratio or one differing there from. Furthermore, the active compounds mentioned can also be present as pure enantiomers or as enantiomer mixtures in any mixing ratio.

In addition, suitable pharmaceutically acceptable salts also refer to salts with bases, e.g. alkali metal (lithium, sodium, potassium) or calcium, aluminium, magnesium, titanium, ammonium, meglumine or guanidinium salts, which also employ bases in salt preparations in an equimolar quantitative ratio or deviations of it.

Based on the novel findings that PDE5 inhibitors improve cerebral vascular reactivity, PDE5-inhibitors are useful in the prophylaxis and/or treatment of diseases, respectively conditions, associated with or based on a impairment or dysfunction of cerebral vascular reactivity and/or neurovascular coupling.

The invention therefore relates to a method of treatment or prophylaxis of a diseases associated with or based on impairment or dysfunction of cerebral vascular reactivity in a patient afflicted with such disease comprising the step of administering a pharmacologically tolerable and therapeutically effective amount of a PDE5 inhibitor to the patient.

Patient in connection with the invention preferably refers to a human.

Cerebral vascular reactivity according to the invention refers to vascular response upon vasodilatory or vasoconstrictory stimuli and/or to regional changes in brain activity (e.g. visual, auditive or sensory stimulation). In particular it refers to microvascular reactivity and neurovascular coupling. Impairment of cerebral vascular reactivity can for example be determined with the transcranial Doppler method as described under examples.

In one possible mode of action according to the present invention the PDE5 inhibitor can improve the cerebral demand-dependent blood perfusion. Since there is a close coupling between cortical vascular activity and neuronal cell-activity, PDE5-inhibitors will thereby improve brain skills as cognition, attention, learning, vigilance, reagibility and endurance.

The invention therefore relates to a method of treatment or prophylaxis of impaired brain skill in a patient which brain skill is selected from the group of cognition, attention, learning, vigilance, reagibility, verbal and visual recognition, concentration capacity, memory retentiveness and endurance. The method is characterized by administering a pharmacologically tolerable and therapeutically effective amount of a PDE5 inhibitor to the patient.

Impairments of cerebral vascular reactivity according to the invention can for example be found in patient groups having one or more of the following conditions: hypercholesterolemia, hypertriglyceridemia, hypertension, pulmonary hypertension, peripheral arterial disease, chronic renal failure, chronic heart failure, diabetes mellitus type II, sepsis, Alzheimer's disease, septic encephalopathy, arteriosclerotic encephalopathy, diabetes associated encephalopathy, toxic encephalopathy, vascular and neuronal dementia, Huntington's disease, Parkinson disease, multiple sclerosis or preeclampsia. Further cognitive impairment can for example be found in hypoxemic patients with chronic obstructive pulmonary disease (COPD) [Antonelli Incalzi et. Al. J Neurol. 2003 March; 250(3):325-32 Cognitive impairment in chronic obstructive pulmonary disease—a neuropsychological and spect study).

Pulmonary hypertension in connection with the invention can refer to primary or secondary pulmonary hypertension. In an embodiment according to the invention pulmonary hypertension refers to chronic pre-capillary pulmonary hypertension.

The invention further relates to a method of treatment or prophylaxis of a diseases associated with or based on impairment or dysfunction cerebral vascular reactivity in a patient suffering from hypercholesterolemia, hypertriglyceridemia, hypertension, pulmonary hypertension, peripheral arterial disease, chronic renal failure, chronic heart failure, diabetis mellitus type II, sepsis, Alzheimer's disease, septic encephalopathy, arteriosclerotic encephalopathy, diabetes associated encephalopathy, toxic encephalopathy (e.g. secondary to liver disease, alcohol abuse or drug abuse), vascular and neuronal dementia, Huntington's disease, Parkinson disease, multiple sclerosis or preeclampsia comprising the step of administering a pharmacologically tolerable and therapeutically effective amount of a PDE5 inhibitor to the patient.

In an embodiment the invention is related to a method of treating impaired cerebral microvascular reactivity in a patient afflicted with pulmonary hypertension, in particular primary pulmonary hypertension.

In an embodiment the invention is related to a method of treating impaired cerebral microvascular reactivity in a patient afflicted with chronic obstructive pulmonary disease (COPD).

In an embodiment the invention is related to a method for treatment of a disease, wherein the disease is associated with pre-senile dementia. Preferably the disease is selected from the group of vascular- and/or neuronal dementia, diabetes associated impairments of neurovascular-coupling, impairments of cerebral vascular function secondary to systemic arterial hypertension and/or arteriosclerosis, Alzheimer's disease, Parkinson disease and Huntington's disease.

In an embodiment the invention is related to a method for treatment of a disease, wherein the disease is associated with or based on post-ischemic disturbances of cerebral function. Preferably the disease is selected from the group of diseases based on cerebral insults, stenosis of extra- or intra-cerebral arteries or cerebral bleeding.

In an embodiment the invention is related to a method for treatment of a disease, wherein the diseases is associated with impairments of cognitive function associated microcirculatory disorders/dysfunction.

In an embodiment the invention is related to a method for treatment of a disease, wherein the disease is selected from the group of septic encephalopathy, arteriosclerotic encephalopathy, diabetes associated encephalopathy, toxic encephalopathy, multiple sclerosis, Creutzfeldt-Jakob disease, encephalopathy associated with autoimmune thyroiditis (Hashimoto's encephalitis), autoimmune thyroiditis, cerebral microangiopathy), hypercholesterolemia, hypertriglyceridemia, hypertension, pulmonary hypertension, peripheral arterial disease, chronic renal failure, chronic heart failure, sepsis, preeclampsia, celiac disease.

A diffuse cerebral dysfunction is often present in sepsis and may ensues even before signs of organ failures. It is better defined as "Sepsis Associated Encephalopathy" (SAE), in order to stress the absence of direct infection of the central nervous system. The main phenotype of SAE is an altered mental status. SAE is potentially reversible, but it always worsens the prognosis. Pathophysiology of SAE is not understood, and might be multifactorial. Indeed, brain dysfunction in sepsis may be related to action of micro-organisms toxins, to the effects of inflammatory mediators, to metabolic alterations and to abnormalities in cerebral circulation. At this moment a specific treatment for SAE does not exist and outcome relies upon prompt and appropriate treatment of sepsis as a whole (Green et al. Sepsis associated encephalopathy (SAE): a review. Front. Biosci. 2004 May 1; 9:1637-41.).

Surprisingly, it has now been found that PDE5 inhibitors can be beneficial in the therapy of SAE.

Thus, in a special embodiment the invention is related to a method for treatment or prophylaxis of sepsis associated encephalopathy (SAE).

The invention further relates to the use of a PDE5 inhibitor for the manufacture of a medicament for the treatment or prophylaxis and/or treatment of diseases associated with or based on impairment or dysfunction cerebral vascular reactivity, in particular for the diseases mentioned above.

As a medicament (also referred to as pharmaceutical preparation hereinafter), the PDE5 inhibitor is either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions. The pharmaceutical preparation of the invention typically comprises a total amount of active compound in the range from 0.05 to 99% w (percent by weight), more preferably in the range from 0,10 to 70% w, even more preferably in the range from 0,10 to 50% w, all percentages by weight being based on total preparation. By the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients, which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents, preservatives, flavours, buffering agents, viscosity-regulating agents, surfactants, adjuvants, binders, lubricants, carriers, diluents, stabilizers, or permeation promoters, can be used.

Tablet formulations for sildenafil, tadalafil and vardenafil are commercially available under the tradenames Viagra®, Cialis® and Levitra® respectively.

The amount of PDE5 inhibitor, or a pharmaceutical acceptable derivative thereof which is required to achieve a therapeutic effect will, of course, vary with the particular compound, the route of administration, the subject under treatment, and the particular disorder or disease being treated. As a monotherapy, a PDE5 inhibitor is generally administered to adult humans by oral administration at a dose of 1 to 100 mg daily. As a monotherapy, sildenafil, vardenafil and tadalafil are generally administered to adult humans by oral administration at a dose of 1-100 mg daily.

Commercially available tablet formulations for sildenafil contain 25, 50 or 100 mg of sildenafil Commercially available tablet formulations for vardenafil contain 5, 10 or 20 mg of vardenafil. Commercially available tablet formulations for tadalafil contain 10 or 20 mg of tadalafil.

Pharmaceutical preparations are often prescribed to the patient in "patient packs" containing the whole course of treatment in a single package. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions and, therefore, lead generally to more successful treatment. It will be understood that the administration of the combination of the invention by means of a single patient pack, or patient packs of each component compound, and containing a package insert instructing the patient to the correct use of the invention is a desirable additional feature of the invention.

PHARMACOLOGICAL EXAMPLES

Example 1

New Pharmacological Mode of Action of PDE5 Inhibitors

It has been shown—contrary to the skilled person's expectation, that the vasodilating effect achieved with a PDE5 inhibitor extends to the improvement of the kinetics in blood flow changes upon stimulation of the cortex by utilizing a visual stimulation paradigm. This could be shown by using the doppler-ultrasound technology which can measure the heart-beat dependent pulsatile blood flow within the basale cerebral vasculature with very high resolution. With a standard visual stimulation the Doppler is able by insonate the posterior cerebral artery to measure the activity-dependent blood-flow-regulation. [Rosengarten et al. (2001) Neurovascular coupling in terms of a control system: validation of a second-order linear system model. Ultrasound Med Biol. 27: 631-5; Babikian et al. (2000) Transcranial Doppler ultrasonography: year 2000 update. J Neuroimaging 10: 101-115]

Example 2

PDE5 Inhibitor for the Treatment of Primary and Secondary Pulmonary Hypertension A pharmaceutical preparation comprising a PDE5 inhibitor can be used to treat patients with primary and secondary pulmonary hypertension. This patients suffer, as our studies with 11 primary pulmonary hypertension patients (diagnosed by chest x-ray, lung function testing, echocardiography, CT-scan of the lung, clinical chemistry, immunological analysis) for the first time clearly demonstrate, from an impairment in the demand-dependent modulation of cerebral blood flow as shown by visual stimulation of the cortex and simultaneous Doppler ultrasound measurements. The hemodynamics aspects of the cerebral blood flow modulation can be described by a mathematical model (see Rosengarten et al., Headache 2003; 43: 458-463). This cited model contains a parameter T which defines the initial fast responding properties of the blood flow upon visual stimulation and three parameters (K, ζ and ω) which define the delayed adjustment of the cerebellar blood flow. T is called the hold-back-time or rate time, K is the gain (which means change in blood flow velocity upon visual stimulation), ζ the attenuation (which represents the dampening due to vessel wall attenuation) and ω the natural frequency (represents the oscillating properties in dynamic neurovascular coupling). Patients with primary and secondary pulmonary hypertension display a pulmonary disturbance between ventilation of the alveoli and their perfusion. Such a demand-dependent inadequate perfusion has also been shown for the vasculature near the muscles. In this invention it is shown that patients with pulmonary hypertension display an increase in the rate time (meaning T is larger) and an enhanced attenuation ζ of the cerebral blood flow within the posterior cerebral artery upon visual stimulation. Thus it is shown that the mentioned disturbed micro-perfusion observed in patients with pulmonary hypertension extents to that of the brain. Treatment of patients with sildenafil (50 mg, oral, one hour before measurement) significantly reduced the attenuation parameter ζ thereby aligning the value of the patients to that of healthy volunteers (see FIG. 1). In addition the pro-longed hold-back time (rate time) in the patients is shortened by treatment with the PDE5-inhibitor sildenafil. This measurements have been performed 1 h after sildenafil intake but all responses to oral sildenafil outlasted 120-150 min.

These effects of sildenafil on visual stimulated cerebral blood flow changes were compared to the effects of the inhaled prostacyclin analogue iloprost, which has recently been shown to improve pulmonary hypertension. In contrast to sildenafil iloprost treatment (2,8 μg inhaled in 4 min) worsens the impaired rate time and attenuation in patients with pulmonary hypertension (FIG. 1).

Thus sildenafil improves the cerebral mal-perfusion with blood through attenuation of an existing endothelial dysfunction under the demand of a stimulatory event for the cortex and is therefore superior over iloprost, which might like sildenafil be used for the treatment of pulmonary hypertension.

Example 3

PDE5 Inhibitor for the Treatment of Septic Encephalopathy

To validate the use of PDE5-inhibitors in the treatment of this disease associated pathophysiology, we use anasthetized rats, which are initially catheterized and artificial respirated. Modulation of the cerebral blood flow evoked by repetitive electrical stimulation of the sole of one foot of the rats is measured by Doppler ultrasound technology as well as the sensoric evoked neuronal potentials (SEPs) by EEG. Baseline measurements are performed before application of LPS to the rats to induce sepsis. 4½ h after inducing sepsis the same parameters (SEP, evoked blood flow) are measured (for the experimental scheme see FIG. 2). LPS induces strong changes in the shape and amplitude of the SEP. Simultaneously the blood flow in the region of the activated neurons is strongly reduced. Surprisingly administration of sildenafil greatly restores the amplitude of the SEP as well as the stimulus induced cerebral blood flow (see FIG. 3)

Figure 1:
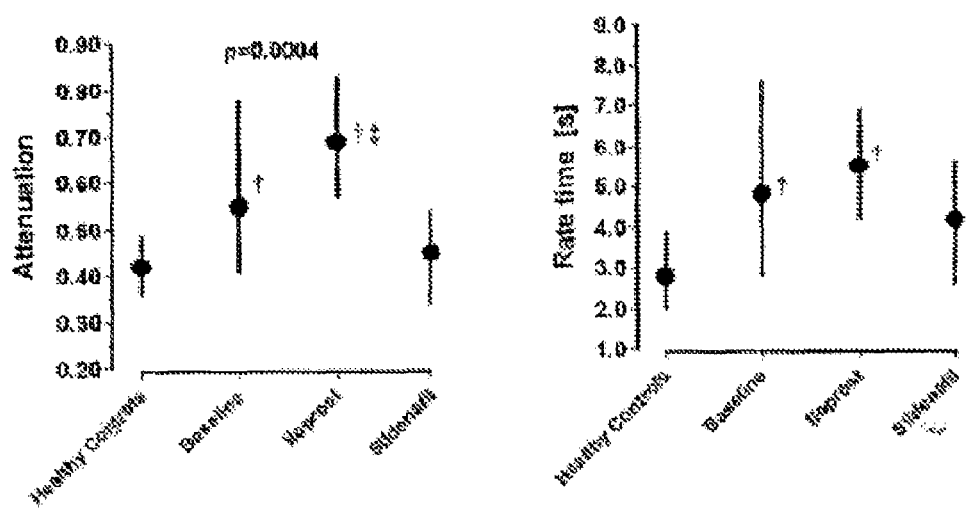
FIG. 1. Assessment of cerebral flow characteristics. Values for rate and attenuation are present in this graph. Medians (filled circles) and 95% confidence intervals (bars) are given for healthy controls, and patients at baseline (untreated), after iloprost inhalation, and subsequent to oral sildenafil intake. Statistical differences were assessed by ANOVA (p-values indicate significant differences between groups). Fisher's post hoc test was calculated at a significance level of $p(0.05;$ †indicates significant differences in comparison to healthy controls, and ‡indicates differences from sildenafil group.
Figure 2:
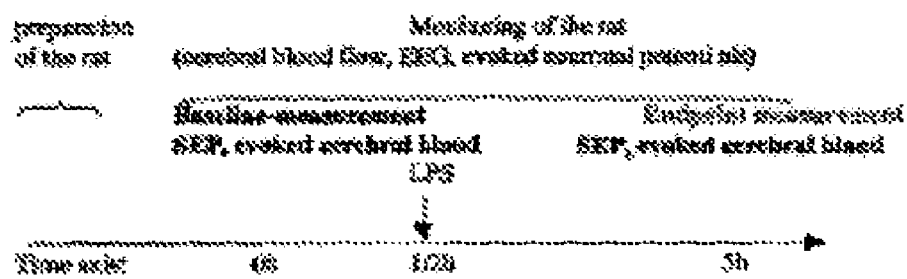
FIG. 2: The experimental scheme
Figure 3:
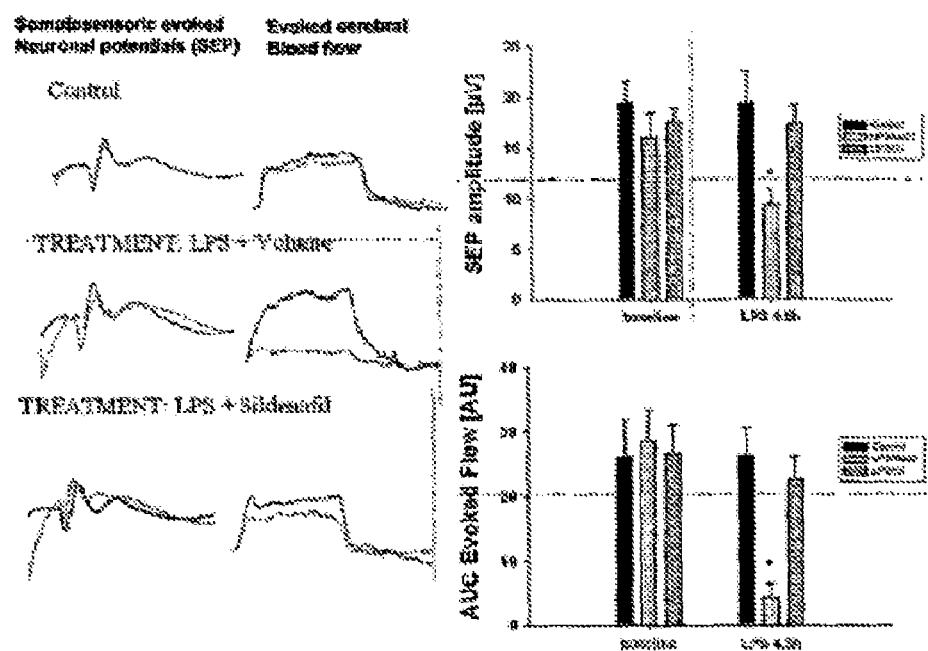
FIG. 3: The effects of LPS and LPS plus sildenafil treatment on somatosensoric evoked neuronal potentials and evoked cerebral blood flow. On the left the black curves show baseline measurement, the grey curves the changes induced by LPS/LPS plus sildenafil treatment. The quantification of the measurements (SEP amplitude and AUC evoked flow) is shown in the right diagrams (Sil=silenafil, LPS=lipopolysaccharide).

The invention claimed is:

1. A method of treatment of sepsis associated encephalopathy in a patient afflicted with such disease comprising the step of administering a pharmacologically tolerable and therapeutically effective amount of 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) or, a pharmaceutically acceptable salt thereof, to the patient.

* * * * *